United States Patent
Guy

(10) Patent No.: US 11,957,926 B2
(45) Date of Patent: *Apr. 16, 2024

(54) TOOTH AND BONE RESTORATION VIA PLASMA DEPOSITION

(71) Applicant: Frederick R. Guy, Syracuse, NY (US)

(72) Inventor: Frederick R. Guy, Syracuse, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 18/093,465

(22) Filed: Jan. 5, 2023

(65) Prior Publication Data

US 2023/0218913 A1 Jul. 13, 2023

Related U.S. Application Data

(60) Continuation of application No. 16/847,264, filed on Apr. 13, 2020, now Pat. No. 11,571,584, which is a continuation-in-part of application No. 16/544,122, filed on Aug. 19, 2019, now Pat. No. 11,642,542, and a continuation-in-part of application No. 15/868,115, (Continued)

(51) Int. Cl.
| | |
|---|---|
| *A61B 18/04* | (2006.01) |
| *A61B 17/56* | (2006.01) |
| *A61B 17/88* | (2006.01) |
| *A61C 5/50* | (2017.01) |
| *A61C 5/62* | (2017.01) |

(Continued)

(52) U.S. Cl.
CPC ............ *A61N 1/44* (2013.01); *A61B 17/56* (2013.01); *A61B 17/88* (2013.01); *A61B 18/042* (2013.01); *A61C 5/50* (2017.02); *A61C 5/62* (2017.02); *A61B 2018/00291* (2013.01)

(58) Field of Classification Search
None
See application file for complete search history.

(56) References Cited

U.S. PATENT DOCUMENTS

| | | | |
|---|---|---|---|
| 4,693,986 | A | 9/1987 | Vit et al. |
| 4,937,928 | A | 3/1990 | Van Der Zel |

(Continued)

FOREIGN PATENT DOCUMENTS

| | | |
|---|---|---|
| EP | 1097692 A2 | 5/2001 |
| KR | 1020060054668 | 5/2006 |

(Continued)

OTHER PUBLICATIONS

Hunger, Fred J., Tagua: The Vegetable Ivory Substitute, from Lathes and Turning Techniques, The Best of Fine Woodworking Magazine (Jul./Aug. 1990). p. 65-67 (Year: 1990).*

(Continued)

*Primary Examiner* — Mohammad M Ameen
(74) *Attorney, Agent, or Firm* — Eschweiler & Potashnik, LLC

(57) ABSTRACT

A natural and sustainable material is derived from the nut of the tagua palm tree that may be fashioned into devices for humans and animals. A pulverized and reconstituted material is disclosed herein that is also treated with a low temperature atmospheric plasma treatment. In an embodiment, a biocompatible carrier gas is ionized to form a biocompatible atmospheric plasma stream. Material, such as nano-scale powdered hydroxyapatite, is introduced into the plasma stream, which is then applied to the natural nut material.

20 Claims, 13 Drawing Sheets

Related U.S. Application Data filed on Jan. 11, 2018, now Pat. No. 10,617,494, said application No. 16/544,122 is a continuation of application No. 14/398,619, filed as application No. PCT/US2014/012576 on Jan. 22, 2014, now Pat. No. 10,384,069, said application No. 15/868,115 is a division of application No. 13/341,584, filed on Dec. 30, 2011, now Pat. No. 9,877,813.

(60) Provisional application No. 61/755,092, filed on Jan. 22, 2013, provisional application No. 61/428,259, filed on Dec. 30, 2010.

(51) Int. Cl.
  *A61N 1/44* (2006.01)
  *A61B 18/00* (2006.01)

(56) References Cited

U.S. PATENT DOCUMENTS

| | | | |
|---|---|---|---|
| 4,917,603 A | 4/1990 | Haack | |
| 5,128,169 A | 7/1992 | Saita et al. | |
| 5,249,964 A | 10/1993 | Levy | |
| 5,378,154 A | 1/1995 | Van Der Zel | |
| 5,609,921 A | 3/1997 | Gitzhofer et al. | |
| 5,871,800 A | 2/1999 | George et al. | |
| 5,873,725 A | 2/1999 | Perler et al. | |
| 6,153,266 A | 11/2000 | Yokogawa et al. | |
| 6,214,368 B1 | 4/2001 | Lee et al. | |
| 6,270,342 B1 | 8/2001 | Neuberger et al. | |
| 6,354,836 B1* | 3/2002 | Panzera | A61C 13/0022 433/223 |
| 7,708,557 B2 | 5/2010 | Rubbert | |
| 7,719,200 B2 | 5/2010 | Laroussi | |
| 7,771,774 B2 | 8/2010 | Berckmans, III et al. | |
| 8,192,835 B2 | 6/2012 | Chi | |
| 8,287,914 B2 | 10/2012 | Riman et al. | |
| 9,131,597 B2 | 9/2015 | Taft et al. | |
| 9,204,950 B2 | 12/2015 | Liu et al. | |
| 9,393,217 B2 | 7/2016 | Hammond et al. | |
| 10,384,069 B2 | 8/2019 | Guy | |
| 11,571,584 B2* | 2/2023 | Guy | A61B 18/042 |
| 2002/0102520 A1 | 8/2002 | Iiyama et al. | |
| 2003/0199866 A1 | 10/2003 | Stern et al. | |
| 2003/0219390 A1 | 11/2003 | Santarpia, III et al. | |
| 2004/0202985 A1 | 10/2004 | Karmaker et al. | |
| 2004/0241613 A1 | 12/2004 | Jansen et al. | |
| 2005/0153069 A1 | 7/2005 | Tapphorn et al. | |
| 2006/0136068 A1 | 6/2006 | de Bruijn et al. | |
| 2006/0210494 A1 | 9/2006 | Rabiei et al. | |
| 2006/0251795 A1 | 11/2006 | Kobrin et al. | |
| 2007/0029500 A1 | 2/2007 | Coulombe et al. | |
| 2007/0160958 A1* | 7/2007 | Belikov | A61C 19/066 433/215 |
| 2007/0173950 A1 | 7/2007 | Zanella et al. | |
| 2007/0259427 A1 | 11/2007 | Storey et al. | |
| 2008/0149566 A1 | 6/2008 | Messersmith et al. | |
| 2008/0280260 A1 | 11/2008 | Belikov et al. | |
| 2009/0142514 A1 | 6/2009 | O'Neill et al. | |
| 2009/0270527 A1* | 10/2009 | Lin | A61K 6/887 523/116 |
| 2010/0047733 A1 | 2/2010 | Nahlieli | |
| 2010/0273129 A1* | 10/2010 | Yu | A61C 5/30 433/217.1 |
| 2010/0324564 A1 | 12/2010 | Bjursten et al. | |
| 2011/0125156 A1 | 5/2011 | Sharkey et al. | |
| 2011/0159273 A1 | 6/2011 | Lukowski et al. | |
| 2012/0052183 A1 | 3/2012 | Wu et al. | |
| 2012/0095558 A1 | 4/2012 | Wooley et al. | |
| 2012/0141775 A1 | 6/2012 | Ahmed et al. | |
| 2012/0171640 A1 | 7/2012 | Guy | |
| 2012/0259272 A1 | 10/2012 | Staack et al. | |
| 2012/0276336 A1 | 11/2012 | Malshe et al. | |
| 2013/0035561 A1 | 2/2013 | Sharkey et al. | |
| 2013/0059273 A1 | 3/2013 | Koo et al. | |
| 2013/0224684 A1 | 8/2013 | Guy | |
| 2013/0253661 A1 | 9/2013 | D'Agostino et al. | |
| 2014/0170410 A1 | 6/2014 | Rupprecht et al. | |
| 2014/0171854 A1 | 6/2014 | Jacofsky et al. | |
| 2016/0106838 A1 | 4/2016 | D'Agostino et al. | |
| 2016/0256607 A1 | 9/2016 | Francis et al. | |
| 2018/0223260 A1 | 8/2018 | Aprikyan et al. | |

FOREIGN PATENT DOCUMENTS

| | | |
|---|---|---|
| KR | 1020110056594 | 5/2011 |
| RU | 2314769 C2 | 1/2008 |
| WO | 2013014212 A2 | 1/2013 |
| WO | 2014116722 A1 | 7/2014 |

OTHER PUBLICATIONS

PCT International Search Authority, International Search Report and Written Opinion, PCT/US2011/060529, dated Jun. 19, 2012 (12 pages).

Eide, Heidi Marie, Non-Final Office Action in U.S. Appl. No. 13/295,248, dated Oct. 29, 2013 (14 pages).

Hunger, Fred, "Tagua: The Vegetable Ivory Substitute," Jul./Aug. 1990, pp. 65-67.

Janick, Jules and Paull, Robert E., "The Encyclopedia of Fruit & Nuts", CAB International, 2008, p. 152.

"Patent Examination Report No. 1 for Australian Patent Application No. 2011325965", dated Nov. 18, 2014, 4 Pages.

"Artificial Teeth", Ann Arbor Argus, Dec. 13, 1895, Retrieved from: http://oldnews.aadl.org/node/135009, 2 Pages.

Ryu, et al., "Mussel-Inspired Polydopamine Coating as a Universal Route to Hydroxyapatite Crystalization", In Advanced Functional Materials, vol. 20, 2010, pp. 2132-2139.

European Patent Office, "Communication Pursuant to Rules 70(2) and 70a(2) EPC for European Patent Application No. 11839111.9", dated Jun. 16, 2015, 10 pages.

European Patent Office, "Supplementary European Search Report for European Patent Application No. 11839111.9", Completion Date: May 19, 2015, 5 pages.

United States Patent and Trademark Office, "Decision on Reconsideration for U.S. Appl. No. 13/295,248", dated May 24, 2017, 9 pages.

United States Patent and Trademark Office, "Decision on Reconsideration for U.S. Appl. No. 13/295,248", dated Feb. 21, 2017, 11 pages.

United States Patent and Trademark Office, "Appeal Decision for U.S. Appl. No. 13/295,248", Mailed Date: Sep. 28, 2016, 26 pages.

Eide, Heidi Marie, "Examiner's Response to Appeal Brief for U.S. Appl. No. 13/295,248", Mailed Date: Jul. 11, 2014, 11 pages.

Eide, Heidi Marie, "Final Office Action for U.S. Appl. No. 13/295,248", dated Apr. 2, 2014, 17 pages.

W.P. Armstrong, "Vegitable Ivory", Noteworthy Plants, Jan. 1999, Retrieved At: <<http://waynesword.palomar.edu/pljan99.htm>>, 10 pages.

dictionary.com, "Denture", Retrieved at: <<http://www.dictionary.com/browse/denture>>, Retrieved Date: Jul. 17, 2017, 3 pages.

Neal, Phillip C., "Interesting Facts in the History of Dentures—Crystal Lake Dentist", Sep. 16, 2011, Retrieved At: <<http://drnealblog.blogspot.com/2011/09/interesting-facts-in-history-of.html>>, 6 pages.

Aponte, Mirayda Arlene, "Restriction Requirement for U.S. Appl. No. 13/341,584", dated Aug. 30, 2016, 6 pages.

Aponte, Mirayda Arlene, "Restriction Requirement for U.S. Appl. No. 13/341,584", dated Oct. 17, 2016, 7 pages.

Ameen, Mohammad M., "Non-Final Office Action for U.S. Appl. No. 13/341,584", dated Mar. 23, 2017, 11 pages.

Ameen, Mohammad M., "Notice of Allowance for U.S. Appl. No. 13/341,584", dated Oct. 2, 2017, 9 pages.

Salvatore, Claudio, "European Search Report for European Patent Application No. 14743617.4", dated Aug. 16, 2016, 7 pages.

Ameen, Mohammad M., "Non-Final Office Action for U.S. Appl. No. 15/868,115", dated May 18, 2018, 14 pages.

(56) References Cited

OTHER PUBLICATIONS

Aparicio, et al., "Variation of Roughness and Adhesion Strength of Deposited Apatite Layers on Titanium Dental Implants", Materials Science and Engineering, vol. C, No. 31, 2011, pp. 320-324.

Kumar CH, et al., "Plasma Torch Toothbrush a New Insight in Fear Free Dentistry", Jun. 20, 2014, 4 pages.

European Patent Office, Communication Under Rule 71(3) EPC for European PAtent Application No. 14743617.4, dated Jan. 9, 2018, 30 pages.

Lucchesi, Nicholas D., "Non-Final Office Action for U.S. Appl. No. 14/398,619", dated Oct. 6, 2016, 10 pages.

Lucchesi, Nicholas D., "Final Office Action for U.S. Appl. No. 14/398,619", dated May 4, 2017, 11 pages.

Lucchesi, Nicholas D., "Advisory Action for U.S. Appl. No. 14/398,619", dated Sep. 26, 2017, 3 pages.

Lucchesi, Nicholas D., "Non-Final Office Action for U.S. Appl. No. 14/398,619", dated Nov. 8, 2017, 11 pages.

Lucchesi, Nicholas D., "Final Office Action for U.S. Appl. No. 14/398,619", dated Aug. 30, 2018, 5 pages.

Lucchesi, Nicholas D., "Advisory Action for U.S. Appl. No. 14/398,619", dated Oct. 24, 2018, 3 pages.

Lucchesi, Nicholas D., "Non-Final Office Action for U.S. Appl. No. 14/398,619", dated Dec. 5, 2018, 5 pages.

Lucchesi, Nicholas D., "Notice of Allowance and Fees Due for U.S. Appl. No. 14/398,619", dated Apr. 3, 2019, 5 pages.

Lucchesi, Nicholas D., "Corrected Notice of Allowability for U.S. Appl. No. 14/398,619", dated Jun. 26, 2019, 2 pages.

Shitov, A., International Search Report for PCT Patent Application No. PCT/US2014/012576, dated May 29, 2014, 2 pages.

Chen, et al., "Histomorphologic Study of the Bone Repair Materials by Using the Cold Plasma Technique", PubMed, PMID: 11774660, vol. 33, No. 5, 1998, pp. 294-296.

Shitov, A., "Written Opinion for PCT Patent Application No. PCT/US2014/012576", dated May 29, 2014, 4 pages.

Becamel, Philippe, "International Preliminary Report on Patentability for PCT Patent Application No. PCT/US2014/012576", dated Jul. 28, 2015, 5 pages.

Ameen, Mohammad M., "Non-Final Office Action for U.S. Appl. No. 16/847,264", dated Mar. 3, 2022, 12 pages.

Ameen, Mohammad M., "Notice of Allowance and Fees Due for U.S. Appl. No. 16/847,264", dated Sep. 23, 2022, 10 pages.

* cited by examiner

Hydroxylapatite

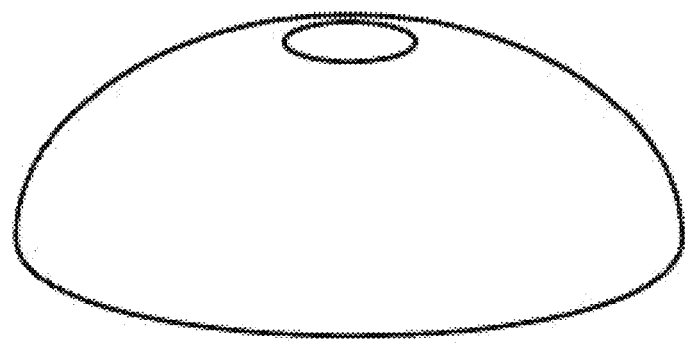
FIG. 17
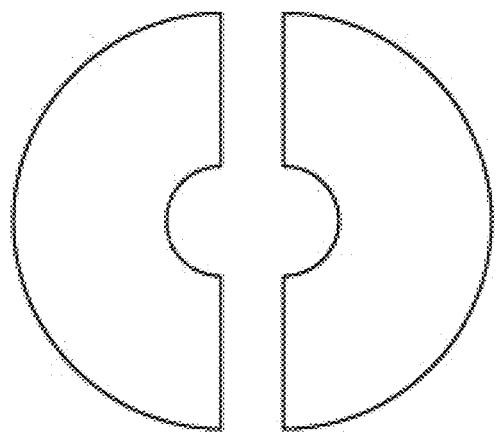 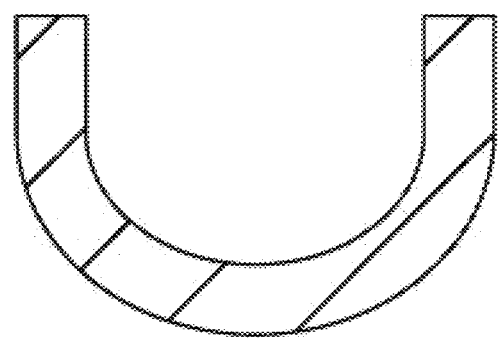
FIG. 18  FIG. 19

TOOTH AND BONE RESTORATION VIA PLASMA DEPOSITION

CROSS-REFERENCE TO RELATED APPLICATIONS

This application is a continuation of U.S. application Ser. No. 16/847,264, filed Apr. 13, 2020, which, in turn, was a continuation-in-part of U.S. application Ser. No. 16/544,122, filed on Aug. 19, 2019, which, in turn, was a continuation of Ser. No. 14/398,619, issued as U.S. Pat. No. 10,384,069, which was a national stage application of PCT/US2014/012576, published as WO 2014/116722, filed Jan. 22, 2014, which, in turn, claimed the benefit of priority to U.S. provisional application No. 61/755,092, filed Jan. 22, 2013, entitled "TOOTH AND BONE RESTORATION METHOD AND DEVICE." U.S. application Ser. No. 16/847,264, filed Apr. 13, 2020, in turn, is also a continuation-in-part of U.S. application Ser. No. 15/868,115, filed Jan. 11, 2018, now patented as U.S. Pat. No. 10,617,494, which, in turn, was a divisional of U.S. Ser. No. 13/341,584, filed Dec. 30, 2011, entitled "Dental Device Material Preparation," issued as U.S. 9,877,813; which, in turn, claimed the benefit of priority to U.S. provisional application No. 61/428,259, filed titled "Method of processing tagua nuts to pre-form material suitable for use in CNC milling machines and for fabrication of natural dental prostheses so that sustainable business practices are supported," filed Dec. 30, 2010. The entirety of each of the foregoing applications is incorporated herein by reference.

BACKGROUND

The present disclosure relates generally to tooth and bone restoration. More specifically, the present disclosure relates to restoring damaged portions of teeth or bone using plasma mediated deposition.

Plasma techniques such as physical vapor deposition or plasma-enhanced chemical vapor deposition are known. Plasma-related techniques have been used in dentistry for sterilization and surface preparation to enhance adhesive properties of dental materials, but have not been used to restore damaged portions of teeth or bone. Other procedures that can halt advancing tooth decay or promote bone recovery, such as periodontal surgery, bone grafts, prosthesis implants, are often difficult, invasive and expensive to implement, and have limited, if any, success in actually restoring bone or enamel.

SUMMARY

The following is a brief summary of subject matter that is described in greater detail herein. This summary is not intended to be limiting as to the scope of the claims.

A non-thermal plasma deposition device, includes an ionization chamber configured to: receive a carrier gas and excite the carrier gas to form an ionizing plasma stream. The ionization chamber further comprises an inlet coupled to a restoration material supply, the inlet intersects with the ionization chamber in a location after the ionizing plasma stream is formed. The ionization chamber is further configured to receive the restoration material and introduce the restoration material into the ionizing plasma stream to form a deposition stream. The deposition nozzle is configured to eject a plume of the deposition stream to deposit the restoration material on an application site. The restoration material is thus deposited on and adhered to the application site via plasma mediated deposition. A shape and mechanical integrity of a damaged portion of a tooth or bone can thus be restored.

In some embodiments, the restoration material is hydroxylapatite ("HAP"), or a derivative thereof. HAP or derivatives thereof are primary constituents of organic bone material. Nano-scale powdered HAP, when deposited via plasma mediated deposition, crystallizes and forms a structure that comports with a crystalline structure of the tooth or bone of the application site.

In some embodiments, a camera disposed proximate to the plume and directed towards the application site is used to capture images of the deposition of restoration material. Not only can such images be recorded for use during diagnosis and comparison, etc., but also such images can be used to provide vision of the deposition when such view may otherwise be obstructed. In some embodiments, an exhaust hood is used to encapsulate the plume and application site. The exhaust structure may be coupled to a vacuum. Surrounding biological material can thus be protected. Residue of the deposition may also be vacated or vacuumed, etc., via an exhaust outlet in the exhaust hood.

A method for repairing a damaged bone or tooth includes exciting a carrier gas to form an atmospheric plasma stream; and either (A) or (B). (A) introducing a restoration material into the plasma stream to form a deposition stream; and depositing the restoration material on an application site by ejecting a plume of the deposition stream to the application site. (B) Depositing the restoration material on an application site; and directing a plasma stream onto the restoration material on the application site. In either case, the application site is a damaged area of a tooth or bone.

A method of repairing teeth or bone, the method includes: affixing biocompatible nano-scale hydroxyapatite onto a damaged portion of a bone or tooth, wherein the hydroxyapatite is adhered via plasma mediated deposition using biocompatible gases, and wherein the plasma mediated deposition is conducted at a biocompatible temperature; and restoring a shape and a mechanical integrity of the damaged portion of the bone or tooth with the hydroxyapatite.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF THE DRAWINGS

FIG. 17 is an exemplary illustration of endosperm of a tagua nut in a shape that conforms generally to the arc and slope of a patient's upper or lower set of natural teeth.

FIG. 18 is an exemplary illustration of a bored endosperm of a tagua nut that is cut in half and prepared for milling.

FIG. 19 is an exemplary illustration of a customized final dental prosthetic.

DETAILED DESCRIPTION

Figure 1:
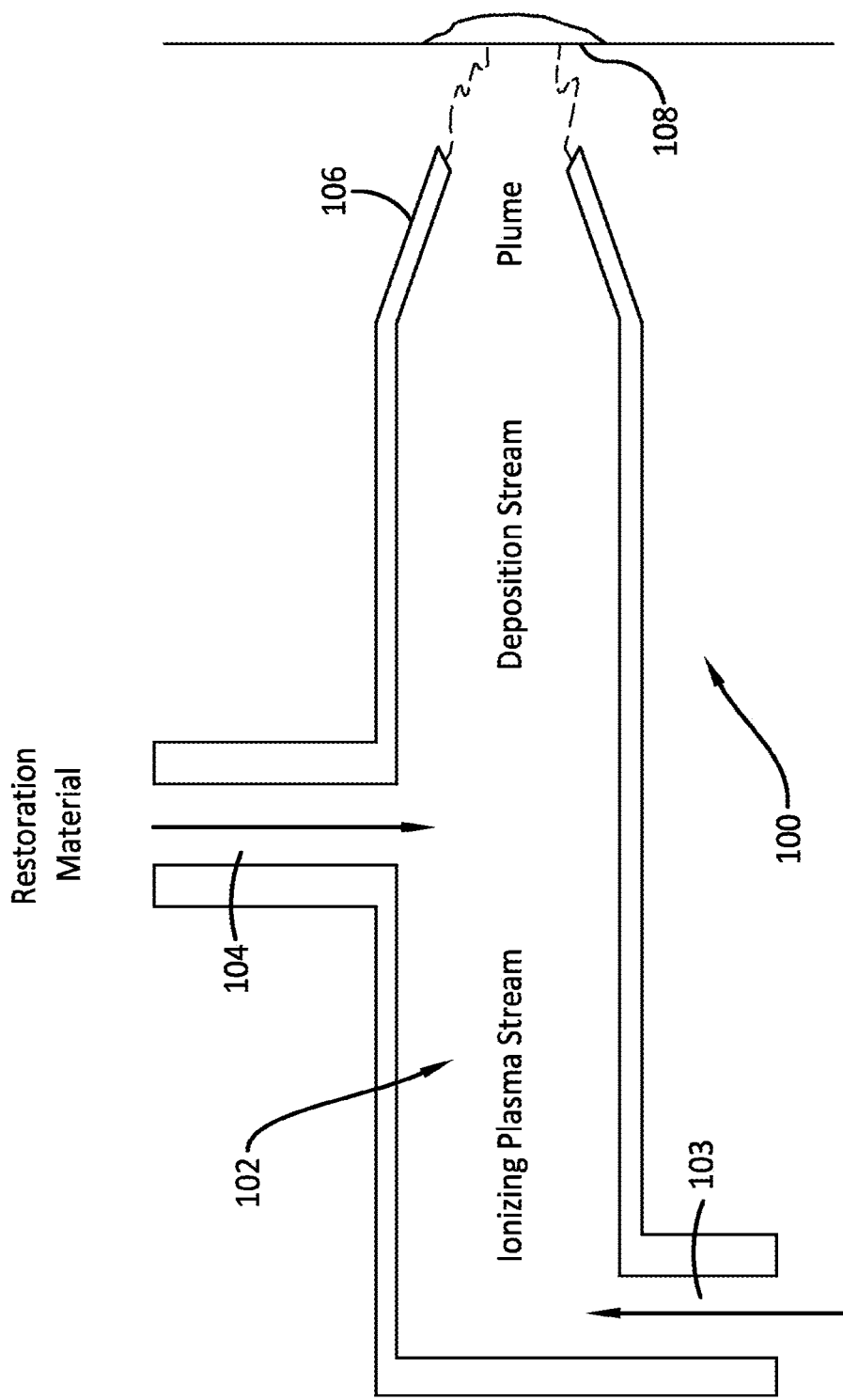
FIG. 1 is a cross-sectional view of an exemplary non-thermal plasma deposition device.

Various technologies pertaining to pulverized tagua materials and restoring damaged portions of tooth or bone using plasma mediated deposition are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, structures and devices are shown in block diagram form in order to facilitate describing one or more aspects. Further, it is to be understood that functionality that is described as being carried out by certain components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. Additionally, as used herein, the term "exemplary" is intended to mean serving as an illustration or example of something, and is not intended to indicate a preference. The articles "a," "an," and "the" should be interpreted to mean "one or more" unless the context clearly indicates the contrary. The term "includes" is used interchangeably with the term "comprising."

Aspects described herein pertain to restoring damaged portions of tooth or bone using plasma mediated deposition. In a general embodiment, a biocompatible carrier gas is ionized to form a biocompatible atmospheric plasma. Restoration material is introduced into the plasma, which is then applied to a damaged portion of a bone or tooth. The restoration material is deposited on and is permanently affixed to the damaged portion of the bone or tooth, thus restoring a shape and mechanical integrity of the bone or tooth.

With reference now to FIG. 1, an exemplary embodiment of a non-thermal plasma ("NTP") deposition device 100 that facilitates restoration of tooth or bone is illustrated. The term "plasma" refers to a partially or wholly ionized gas composed essentially of photons, ions and free electrons as well as atoms in their fundamental or excited states possessing a net neutral charge. Plasma possesses a net neutral charge because the number of positive charge carriers is equal to the number of negative ones. An NTP refers to a plasma that is near ambient temperature (e.g., from 20° C. to 60° C., or 25° C. to 40° C., or 22° C. to 30° C.) that is obtained at atmospheric or reduced pressures. For example, remote treatment, direct treatment, or electrode contact NTP may be used, also, afterglow or active plasma methods may be used. In one embodiment at least a partial vacuum is applied to enhance the process. In an embodiment, the plasma deposition process does not include sputtering processes. In an embodiment of the device and process described herein plasma polymerization occurs where the restoration material is a polymerizable material (or monomer) that is introduced into the plasma stream.

As shown in FIG. 1, the NTP deposition device 100 comprises an ionization chamber 102 that is configured to receive a carrier gas and excite the carrier gas to form an ionizing plasma stream. The ionization chamber 102 further comprises carrier gas inlet 103, and a restoration material inlet 104 that is configured to receive a restoration material, such as a bone or tooth restoration material, and introduce the restoration material into the ionizing plasma stream to form a deposition stream. The inlet 104 is coupled to the ionization chamber 102 and is disposed along a length of the ionization chamber 102. The interior of the inlet 104 intersects with the interior of the ionization chamber 102 in a location between the ionizing plasma stream and a deposition nozzle 106. The intersection is after the ionizing plasma stream has been activated. In an embodiment utilizing internal electrodes the inlet 104 is placed away from the electrode gap, such as at least 0.25 mm, at least 1 mm, or at least 5 mm from the electrode gap. A deposition nozzle 106 is configured to receive the deposition stream, and shape a plume of the deposition stream to conform to a desired application site 108. The deposition nozzle 106 directs the deposition stream onto the application site 108 and deposits the restoration material onto the application site 108 via plasma mediated deposition of the plume of the deposition stream.

In an embodiment, the NTP deposition device 100 is dimensioned to be handheld and light enough for easy manipulation in small work areas such as a patient's mouth or a surgical incision. Form-factors similar to an endoscope or a wand used in 3-D imaging for dentistry may be utilized.

The carrier gas is a biocompatible gas that is not harmful to tooth, bone, or surrounding biological tissue. The carrier gas can comprise, for example, helium, oxygen, nitrogen, argon, ambient air, or combinations thereof. In an embodiment, the carrier gas is a non-reactive gas. Carrier gas is introduced into the ionization chamber 102 from a supply such as a pressure vessel or supply feed. A flow rate of the carrier gas into the ionization chamber 102 can be controlled by, for example a valve. For example, the flow rate of the carrier gas into the ionization chamber can be restricted to 5 mL per minute to 15 L per minute, such as 500 mL per minute to 10 L per minute, or 1 L per minute to 5 L per minute. A desired flow rate for the carrier gas may depend on desired characteristics of the ionizing plasma stream as well as characteristics of the ionization chamber 102.

The ionization chamber 102 excites the carrier gas to form the ionizing plasma stream. For example, subjecting the carrier gas to high energy ultraviolet light, (e.g., radiation having a wavelength between 180 nm to 270 nm), microwaves (e.g., radiation having a frequency of 2.4 GHz or more), or an electric discharge with a high voltage difference can result in the formation of an ionizing plasma. In an example, the ionization chamber 102 comprises a pair of electrodes, or an electrode and a grounded connection, which creates a voltage difference across the carrier gas within the ionization chamber 102. A current source, such as a 10 kHz, 20 kHz, or 40 kHz, or alternating current, can be used to drive the voltage difference. The voltage difference needed to excite the carrier gas may depend on the carrier gas selected, a shape of discharge needle, and an impedence matching network of the NTP deposition device 100, and other factors.

In an embodiment the plasma source is a capacitively coupled radio frequency (13.56) MHz discharge created the tip of a sharp needle.

While electron temperature may be very high, due to the excitation, the macroscopic temperature of the ionizing plasma stream remains close to room temperature. This is because of low power consumption (e.g., 100 mW), convective cooling, and/or a small volume size of plasma ejected by the NTP deposition device 100. The plasma ejected from the NTP deposition device 100, the "plume," has a small volume, (e.g., 0.01 mm$^3$ to 2 mm$^3$, 0.1 mm$^3$ to 1 mm$^3$, or 0.5 mm$^3$ to 1.5 mm$^3$) and a relatively large surface to volume ratio, which promotes energy escape by thermal diffusion.

The inlet 104 in the ionization chamber 102 is also in communication with a feed of restoration material. In an embodiment, the inlet 104 is coupled to a container with a supply of restoration material that may be pressurized, for example, the restoration material may be pumped, pushed, or gravity fed into the inlet 104. In an example, the restoration material is aerosolized with a gas such as a carrier gas before being fed into the inlet 104.

The restoration material is a material that, when deposited on and affixed to tooth enamel, dentin, or bone, crystalizes and adheres to crystalline elements of the tooth enamel, dentin, or bone. By depositing the restoration material on a damaged portion of enamel, dentin, or bone, the damaged portion may thus be restored. In an embodiment, the restoration material is a nano-scale powder suitable for being introduced into the ionizing plasma stream. The restoration material can comprise a variety of materials such as HAP, nano-scale diamonds, calcium apatite, or other minerals or materials. In an embodiment, the restoration material is exclusive of zircon-oxide, poly(methyl methacrylate), polyethylene, metal, or glass.

Calcium apatite, $Ca_5(PO_4)_4(R)$, where R is an end-member, is a mineral produced and used by biological microenvironment systems. Species of of calcium apatite include hydroxylapatite, $Ca_5(PO_4)_4(OH)$ ("HAP"), flourapatite, $Ca_5(PO_4)_4(F)$, and chlorapatite, $Ca_5(PO_4)_4(Cl)$. Portions of bone material comprise HAP wherein many of the OH groups are missing and contain many carbonate and acid phosphate substitutions. In an example, the restoration material is a nano-scale powder of HAP, carbonated calcium-deficient HAP with acid phosphate substitutions, or derivatives or substitutions thereof. In an embodiment, the manufactured nano-scale powders are dimensioned to approximately match a size of naturally occurring tooth enamel and bone crystals, for example 500 nm to 40 micrometers, such as 1 micrometer to 20 micrometers, or 2 micrometers to 10 micrometers. Thus, when deposited via plasma mediated deposition, the size of the nano-scale powder may promote crystallization of the restoration material that conforms with a crystalline structure of tooth enamel or bone. The restoration material should have ionic bonding qualities needed to achieve a non-toxic, biocompatible, permanent reconstruction of tooth and/or bone. It was also surprisingly found that the NTP deposition process causes additional crystallization in the restoration material.

Introducing the restoration material via the inlet 104 into the ionizing plasma stream in the ionization chamber 102 forms a deposition stream. The deposition nozzle 106 receives the deposition stream, and shapes the plume of the deposition stream to conform to a desired application site 108. The plume is ejected proximate to the application site, thus depositing bone restoration material on the application site. A distance between the deposition nozzle 106 and the application site is selected such that bone restoration material adheres to, but does not damage the application site. Such distance may be calibrated based on, for example, a flow rate of the carrier gas, a flow rate of the restoration material, a size of the application site, and/or other factors. Example distances from the nozzle tip to the application site 108, include 0.001 mm to 5 mm, 0.01 mm to 3 mm, or 0.1 mm to 1.5 mm.

While the deposition stream is at a temperature that is not harmful to biological material, it may be desirable to deposit restoration material on the application site 108 exclusive of any surrounding biological material. Thus, in an embodiment the deposition nozzle 106 is configured to adjust a size and shape of the plume of the deposition stream.

In an embodiment, the inlet 104 may be external and intersect with the plasma stream after it passes through the deposition nozzle 106.

A desired application site 108 may be, for example, a dental cavity, a bone fracture, a bone spur, a weakened or damaged portion of a tooth or bone, a degenerated disk, an arthritic joint, a void (or chip) in a tooth or bone, a groove in a teeth, such as may be caused by severe bruxism, or a combination thereof.

For treatment of bone damage, surgical techniques such as arthroscopic surgery may be adapted for use with the device 100.

Figure 2:
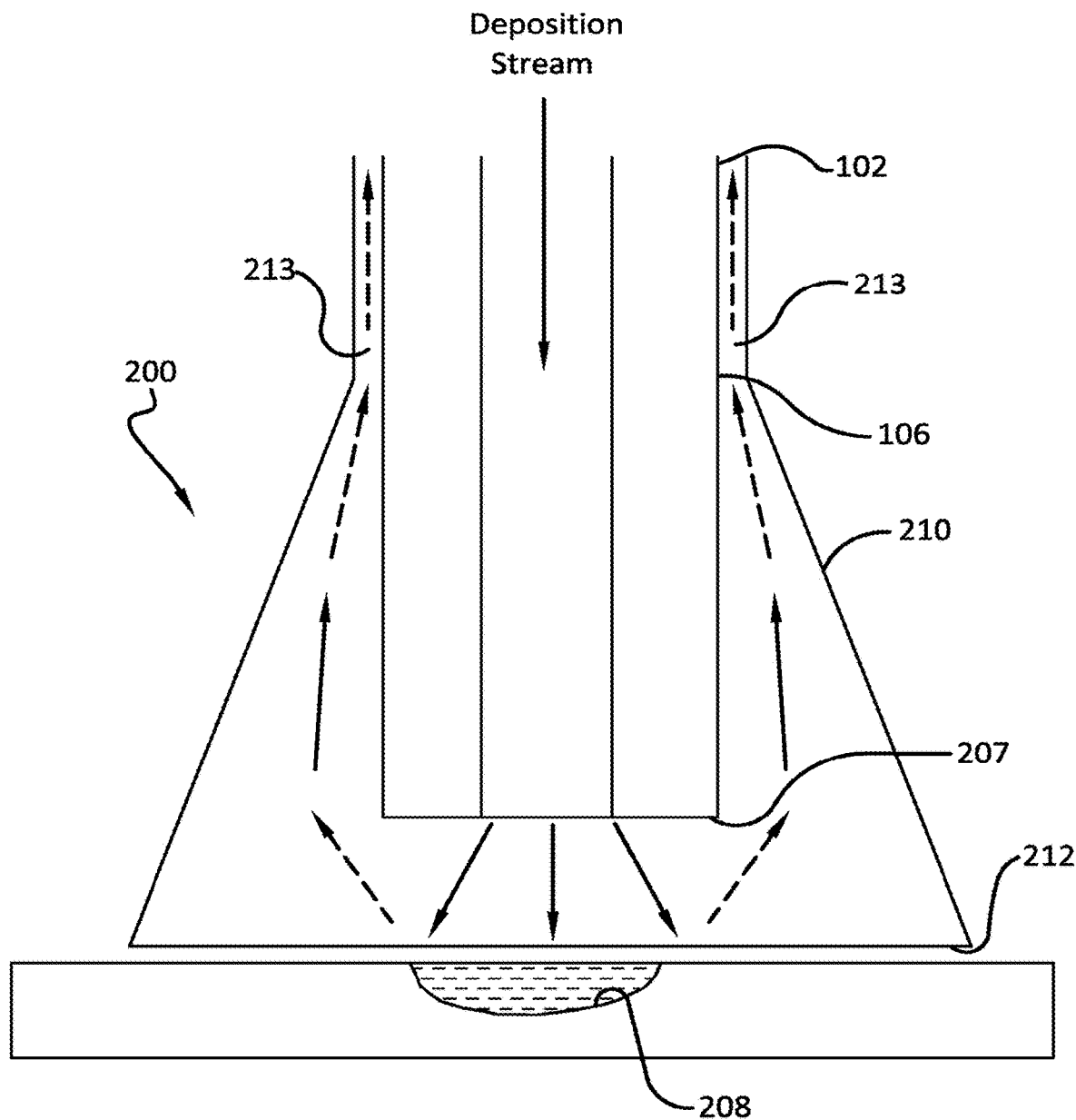
FIGS. 2 and 3 are flow diagrams of exemplary methodologies that facilitate restoring tooth or bone via plasma mediated deposition of restoration material.

In an embodiment depicted in FIG. 2, an NTP deposition device 200 further comprises an exhaust hood 210 configured to vacate residue of the deposition stream from the application site 208 (which in this case is depicted as a cavity on a tooth surface) and/or provide at least a partial vacuum in the volume that is encompassed by the exhaust hood 210 and near the application site 208. Depending on the strength of the vacuum, the volume under vacuum may extend from a terminal circumferential edge 212 of the exhaust hood 210 from 0.001 mm, to 5 mm, such as 0.01 mm to 2 mm, or 0.1 mm to 1 mm.

In an example, the exhaust hood 210 uses suction or a vacuum to extract the residue. The exhaust hood 210 may be a cup, hood, skirt, funnel or another structure configured to encapsulate the deposition nozzle 106 and cover over the application site 208 so as to capture restoration material that does not adhere to bone or tooth and/or the ionized gasses in the deposition stream. The exhaust hood 210 may comprise a rigid or flexible material. For example, the material may be a soft elastomeric material, a hard plastic material, a rigid metal material, or a soft, but stiff elastomer that will hold its form under vacuum, but will conform to the application site 208 if pushed against it.

In an embodiment, the exhaust hood 210 is co-axial with and coupled to the ionization chamber 106 or deposition nozzle 206 and circumscribing an area centered about the deposition nozzle 106. A terminal circumferential edge 212 of the exhaust hood 210 may extend 0.1 mm to 5 mm in radius about the deposition nozzle 106, such as 0.5 mm to 2 mm, or 1 mm to 1.5 mm. The terminal circumferential edge 212 may extend to be coplanar with a terminal end of the deposition nozzle 207, or extend within 10 mm past a plane with the terminal end of the deposition nozzle 207, such as 0.5 mm to 5 mm, or 1 mm to 1.5 mm.

The terminal circumferential edge 212 of the exhaust hood 210 can be placed against the application site 208 so that the deposition nozzle 106 and the plume are substantially or completely encapsulated. In an embodiment, the circumferential edge 212 of the exhaust hood 210 is from 0.001 mm to 5 mm in proximity to the application site 208, such as 0.01 mm to 2 mm, or 0.1 mm to 1 mm. In an embodiment, the circumferential edge 212 rests against the surrounding tissue or area around the application site 208.

In an embodiment, the exhaust hood 210 is moveable in an axial direction along the outer surface of the ionizing chamber 102 and deposition nozzle 106. For example, the exhaust hood 210 may be coupled to the ionizing chamber 102 through a sliding mechanism or a sliding and locking mechanism. In FIG. 2, the exhaust hood 210 is concentrically fitted slideably coupled around the ionization chamber 102 and nozzle 106.

In an embodiment, a tightened screw locking mechanism, such as a thumb screw, may be coupled to the exhaust hood 210 and may be tightened against the ionization chamber 102 and untightened to lock and unlock the slideable coupling. In another embodiment, the locking mechanism may be a tooth-in-groove structure or a reciprocating ratcheting mechanism. In an embodiment the exhaust hood 210 can be coupled to the ionizing chamber 102 through a tight fitting cap or ring that is slideable along the outer surface of the ionizing chamber 102. In an embodiment, the exhaust hood 210 is also configured to be locked into an axial position to prevent unwanted movement. This may be accomplished by known locking mechanisms for axially moveable parts, such as an insertable pin or lever that arrests movement in the axial direction. Axial rotation may also be prevented by known mechanisms including levers, pins, or detents.

The vacuum exhaust outlet 213 is shown as extending up along the side of the ionization chamber 102. The exhaust outlet may circumscribe the entire lower portion of the ionization chamber 102 or only partially circumscribe a portion of it. In other embodiments, the exhaust outlet 213 is coupled to the exhaust hood 210 near the circumferential edge 212 of the exhaust hood 210, such as 0.01 mm to 3 mm, 0.1 mm to 2 mm, or 0.5 mm to 1.5 mm from the circumferential edge 212 of the exhaust hood 210.

The exhaust outlet 213 is in communication with a vacuum device, such as an electric powered vacuum mechanism, or other known vacuum device. In an embodiment, the vacuum suction power (or pressure) is adjustable to levels desired to produce a vacuum that removes loose material and/or reduces heat build-up in the affected area. In an embodiment, the vacuum power is limited to a pressure that is less than a power that would disrupt the restoration material that is deposited onto the application site 208. In an embodiment, the vacuum power is high enough to affect the plasma deposition process, as certain plasma deposition processes may be enhanced in a vacuum environment. In an embodiment, the vacuum power is enough to remove debris, but has no effect on the deposition process. In an embodiment, the vacuum provides a drop from 99% to 1% of atmospheric pressure, e.g. (1 atm), such as 95% to 50%, or 90% to 75% of atmospheric pressure.

The exhaust hood 210 may be adjustable so that the diameter of at least portions of the exhaust hood 210, including the terminal circumferential edge 212, can be increased or decreased. This may be accomplished by using a structure similar to a camera aperture. Where multiple overlapping curvilinear panels are utilized to form the hood structure. In an embodiment, the exhaust hood 210 may be removable and replaceable with exhaust hoods of various shapes and features to adapt device 200 to the shape and conditions of the affected tooth, bone, or surrounding area. For example, the edge of a tooth, such as a bicuspid, may benefit from having an extended piece that wraps around the side of the tooth and where the vacuum exhaust outlet 213 is below the level of the application site 208 or to the side of the application site 208.

In an alternate embodiment, a structure similar to the exhaust hood 210, such as a protective hood, is coupled to the NTP deposition device 200, but does not include any exhaust outlet 213 or vacuum mechanism. In this embodiment the protective hood operates to merely protect surrounding tissue from deflected deposition material and heat. This option may be useful for operating on an application site that is locally numbed, if proper care is taken. The protective hood may also be combined with the camera and adjustability features described herein.

Figure 3:
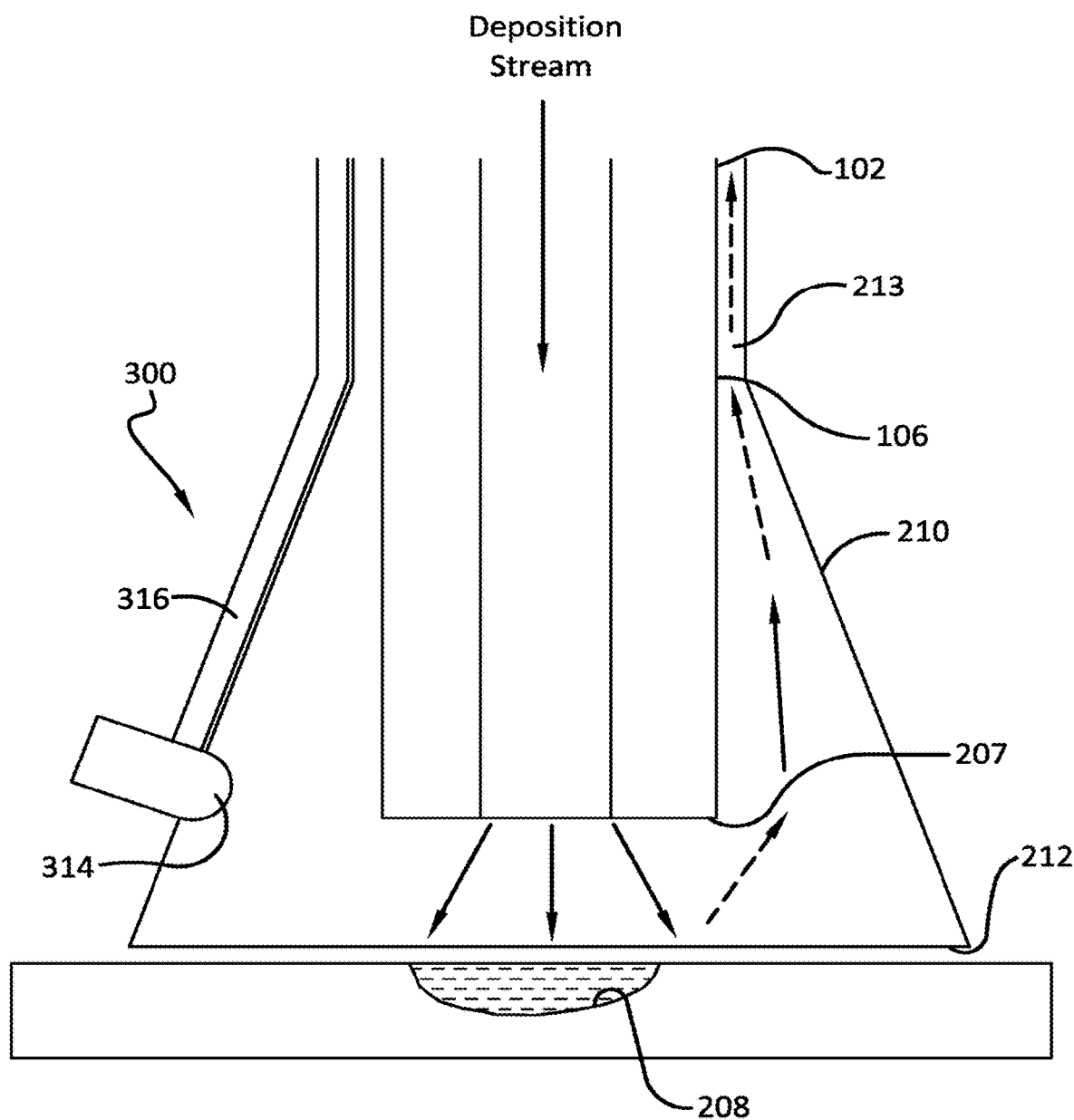

In another embodiment, shown in FIG. 3, an NTP deposition device 300 can further comprise a camera 314 configured to capture images of the deposition of the restoration material on the application site 308 (in this example a bone surface with a chip or fracture). The camera 314 may capture still or moving images of the deposition of the restoration material. Captured images may be used to show a before/after change resulting from the deposition, or may be used in diagnosis or patient evaluation. Additionally, captured images can be used to provide the operator of the NTP deposition device 300, such as a dentist, orthodontist, or surgeon with additional vision during the deposition process. In an example, a portion of the application site 308 may be obstructed from view of an individual using the NTP deposition device 300 by teeth, bone, other biological material, or the exhaust hood 210. An obstructed view can inhibit the accuracy, efficiency, and precision of the deposition, and can lead to waste of materials such as carrier gas and/or restoration deposition material.

Images captured from the camera 314 disposed on the NTP deposition device 300 can, for example, be transmitted to and displayed on a video display visible by the operator using the NTP deposition device.

In an embodiment, at least a portion of the camera 314 is disposed within the exhaust hood 210. As the exhaust hood 210 may obstruct the application site 308, disposing the camera 314 within the exhaust hood 210 enables vision of the application site 308 while protecting surrounding biological material and evacuating residue of the deposition. Wiring or optical cables 316 for the camera 314 may run closely along the exterior of the device 300.

In an embodiment, the camera 314 may be disposed opposite an exhaust outlet 213 within the exhaust hood 210 so as to reduce an amount of residue build-up on the camera 314.

Figure 4:
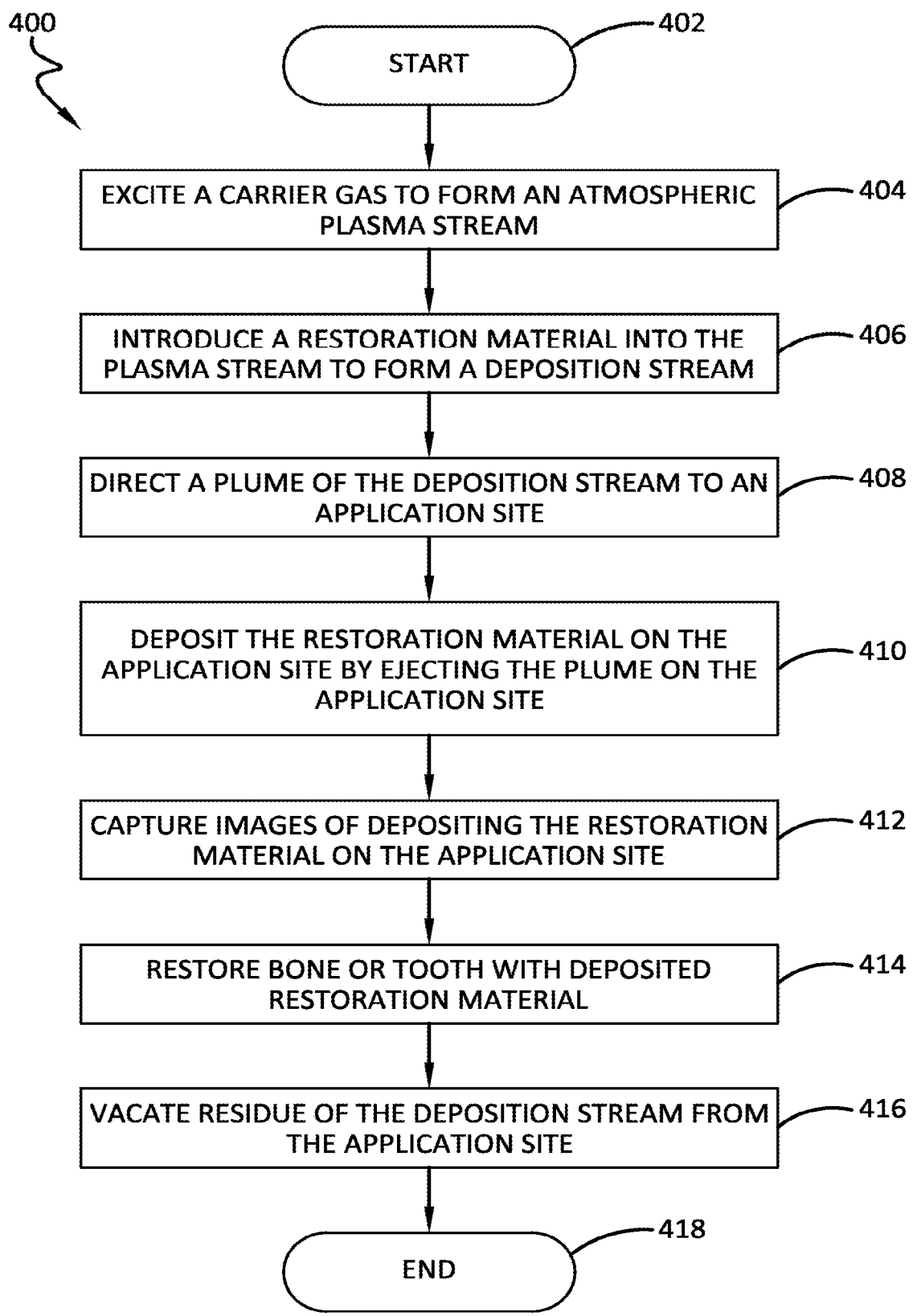
FIG. 4 is a cross-sectional view of an embodiment of the plasma deposition device with an exhaust structure.
Figure 5:
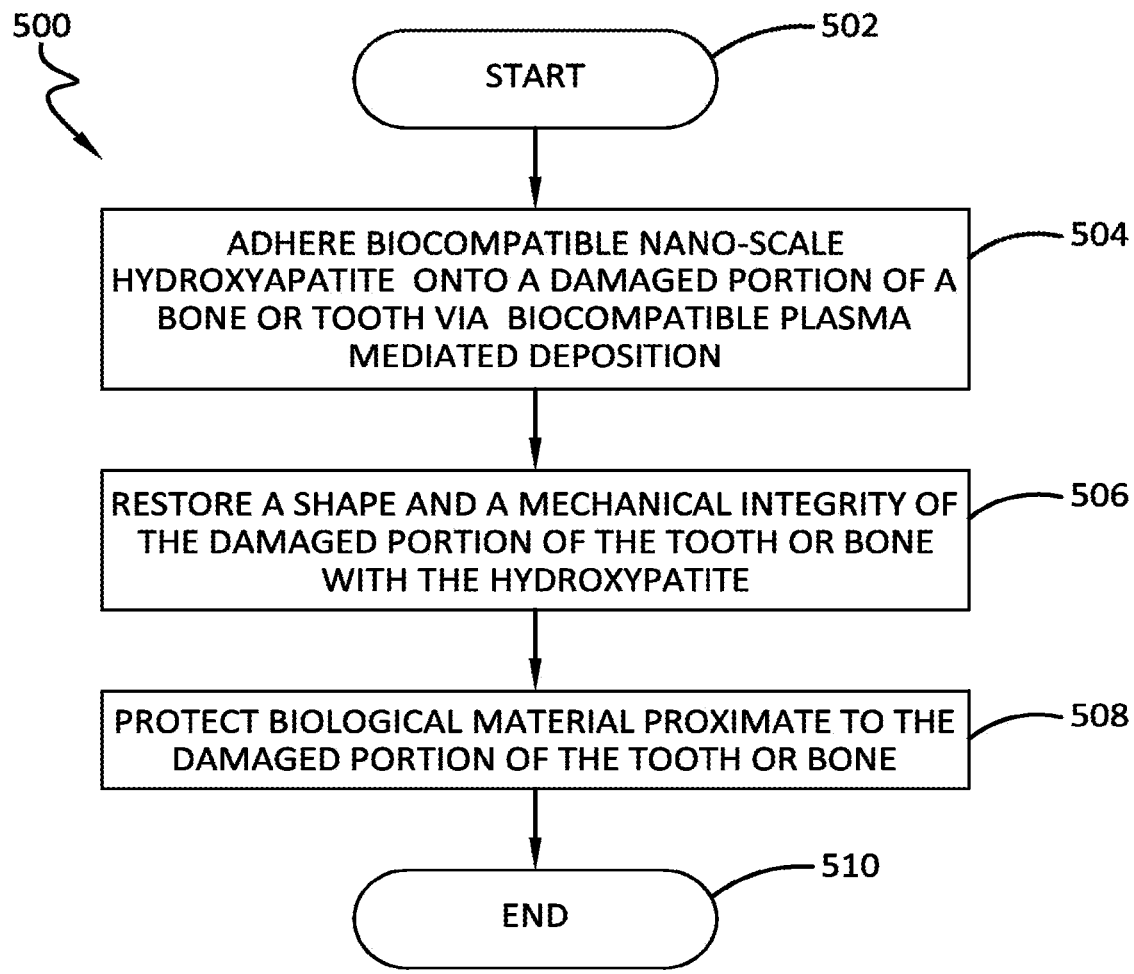
FIG. 5 is a cross-sectional view of an embodiment of the plasma deposition device with a camera and an exhaust structure.

With reference now to FIGS. 4 and 5, various exemplary methodologies are illustrated and described. While the methodologies are described as being a series of acts that are performed in a sequence, it is to be understood that the methodologies are not limited by the order of the sequence. For instance, some acts may occur in a different order than what is described herein. In addition, an act may occur concurrently with another act. Furthermore, in some instances, not all acts may be required to implement a methodology described herein.

Referring now to FIG. 4, an exemplary methodology 400 that facilitates restoring bone, enamel, or combinations thereof via atmospheric plasma mediated deposition is illustrated. The methodology 400 starts at 402, and at 404 a carrier gas is excited to form an atmospheric plasma stream. The carrier gas is a biocompatible, non-toxic gas, and can be excited via various techniques such as, for example, being exposed to a voltage difference across an ionization chamber. At 406, a restoration material is introduced into the plasma stream to form a deposition stream. The restoration material is as described above, a material that, when deposited on tooth or bone, crystallizes with a structure that comports with a crystalline structure of the tooth or bone. In an example, the restoration material is a nano-scale powder of hydroxyapatite. The restoration material may be introduced into the plasma stream via a variety of techniques such as, for example, spraying, aerosolizing, or mixing.

At 408, a plume of the deposition stream is directed to a desired application site. In an example, a nozzle shapes the plume to a size suitable for a particular application site such that surrounding biological material is protected from the deposition stream. At 410, restoration material is deposited on the application site by ejecting the plume proximate to the application site.

Optionally, at 412, images of depositing restoration material on the application site are captured. Such images may be captured, for example, by a camera directed towards the application site and disposed proximate to the plume.

At 414, bone or tooth damage at the application site are restored with the deposited restoration material. Restoration of the application site may include filling a void, such as a fracture, indentation, or crack back to its original state. For example, this may include filling the void up to a plane running across the highest edges of an indentation, fracture, or crack and possibly slightly exceeding the plane to substantially restore the original shape. For example, a crack may be filled within 10%, such as within 5%, or 2% of its volume or its distance over or beneath the plane.

In an embodiment, the restoration is not a mere thin coating on the surface of the application site, nor is it an adhesive by which additional material is added. Rather, the restoration deposition has a substantial thickness and fills up a voided area that has suffered the loss of original material that has abraded, broken, or otherwise decayed away. In an embodiment, the restoration deposition has a thickness of 0.001 mm to 35 mm, 0.1 mm to 5 mm, or 10 mm to 25 mm.

Optionally, at 416, residue of the deposition stream is vacated from the application site. The residue may be vacated by, for example, an exhaust hood, or vacuum, etc., disposed proximate to the plume. Residue may include, for example, excess restoration material, heat, and/or carrier gas. The methodology ends at 418.

Referring now to FIG. 5, an exemplary methodology 500 that facilitates restoring a shape and mechanical integrity of a damaged portion of tooth or bone with hydroxyapatite is illustrated. The methodology 500 starts at 502, and at 504, biocompatible nano-scale hydroxyapatite is adhered onto a damaged portion of a bone or tooth via biocompatible plasma mediated deposition. At 506, a shape and mechanical integrity of the damaged portion of tooth or bone is restored with the hydroxyapatite. At 508, biological material proximate to the damaged portion of tooth or bone is protected from the plasma mediated deposition. The methodology ends at 510.

In an embodiment of this method 500, the restoration material is introduced after the deposition nozzle. For example, the restoration material may be deposited via a solution onto the application site and then ionized by the plasma gases that have no deposition material directly in the stream.

In an embodiment, a system or kit comprises a non-thermal plasma deposition device as disclosed herein. The system or kit also comprises one or more of the following: a restoration material, a supply container for the restoration material, a biocompatible carrier gas supply, a biocompatible carrier gas, an exhaust hood, a protective hood, a camera for capturing images of the restoration material deposition, a display for displaying the camera images, a vacuum device, a pressurization device, and conduits or wiring for connecting any of the components listed herein. The kit or system may be utilized to operate the methods for tooth or bone restoration disclosed herein.

In an embodiment, a naturally-derived material obtained from sustainable resources, such as tagua may be used with the non-thermal plasma deposition technique and device.

The naturally derived materials obtained from sustainable resources has physical characteristics providing durability, texture, color and shading that match natural teeth. The natural materials are sufficiently workable when using normal manufacturing techniques and equipment routinely applied for making currently available dental devices comprising non-natural or sustainable materials such as metal and ceramics. The devices include those selected from the group consisting of bridges, full dentures, partial dentures, crowns, caps and combinations thereof. The aforementioned dental devices are currently made from a number of materials that provide sufficient durability to sustain the rigors of chewing as well as provide good cosmetic aesthetics to match the remaining natural teeth in terms of physical factors including, but not necessarily limited to shape, size, texture and color. Currently the materials used to make such devices include non-sustainable precious metals such as gold, ceramics, porcelain, plastics or composites of these materials. Standard dental devices are typically made of the above materials with a uniform high degree of hardness throughout the material. Unlike natural teeth which consist of multiple layers of organic and mineral material in an ascending degree of hardness, from root to dentin to enamel, which has both formal and functional qualities and characteristics. Those qualities and characteristics are perfectly adapted to provide a kind of cushion or shock absorbing effect which protects the surrounding maxillofacial structure from stress-induced damage. Such damage can include serious bone, muscular, and nerve damage, which is more likely to occur when superfluously hard and rigid dental prosthetics, replace natural teeth which have a shock absorbing quality.

The naturally-derived material disclosed herein provides a natural, agriculturally derived solution that has substantially the same variable component hardness, and cushioning effect, as natural teeth.

Figure 8:
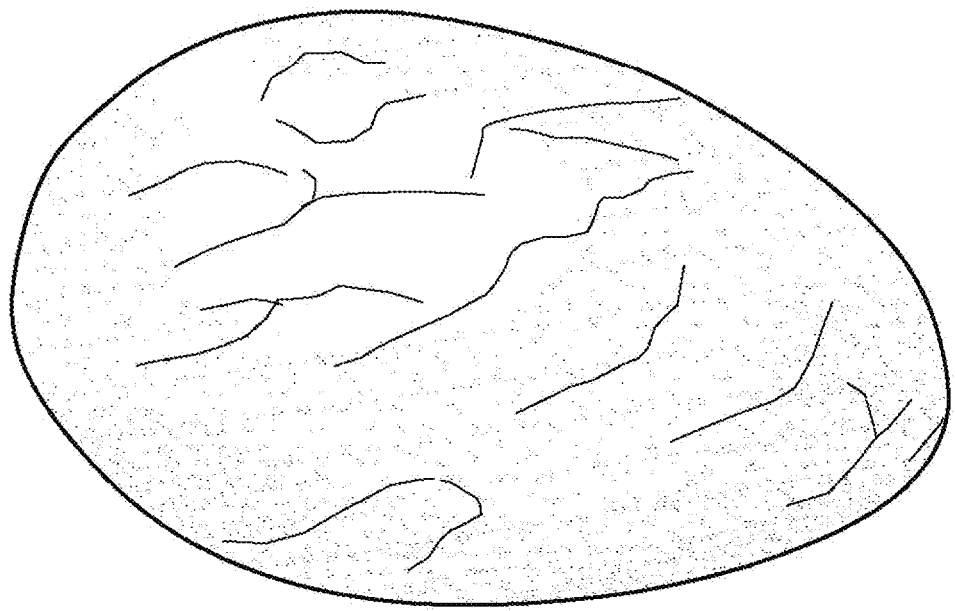
FIG. 8 is a perspective view of an example Tagua Nut.

In an embodiment, the dental device material comprises dehydrated and hardened endosperm of the nut of the Tagua palm, a species of the genus *Phytelephas* FIG. 8. *Phytelephas* is a genus containing six species of palms (family Arecaceae), occurring from southern Panama along the Andes to Ecuador, Bolivia, and Peru. They are medium-sized to tall palms reaching 20 meters tall, with pinnate leaves. They are commonly known as Tagua palms. In its original state, the "nut" is covered with pericarp. The nut is covered with a brown, flaky skin and shaped like a small avocado, roughly 4-8 cm in diameter. Since the nut has a protective husk or shell, once the nuts are harvested there are no extreme inspection, sorting and handling steps that must be taken to sort the nuts before processing. This material is harvested by the usual manual or machine harvesting methods generally known in the art.

The dehydrated Tagua nut material's texture, color and shading vary over the range normally associated with natural teeth. To that end, the desired shading and color of the material is selected individually for the patient prior to manufacturing the device. Furthermore, the color of the material can be modified by routine methods known in the art for bleaching material or foods such as wheat flour. Additionally, the texture of the material may be manipulated to create a consistent surface of the device that matches the natural teeth to avoid preoccupation by the patient's tongue.

Figure 9:
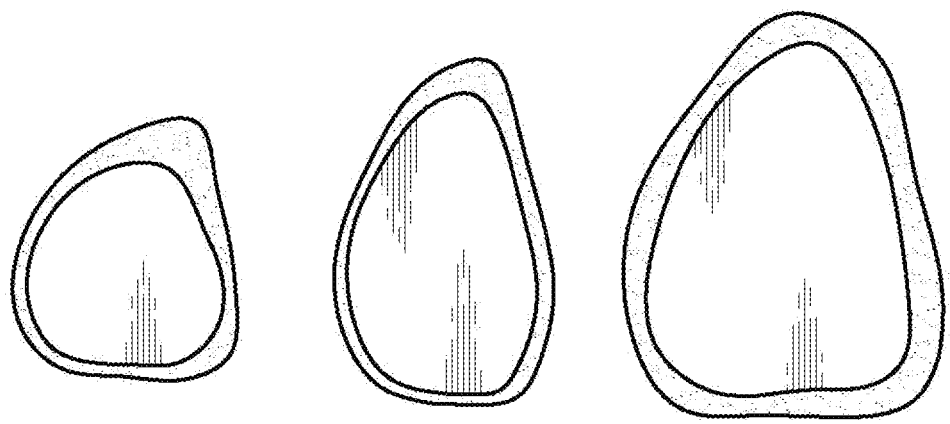
FIG. 9 is a cross-sectional view of examples of a Tagua Nut Endosperm.
Figure 11:
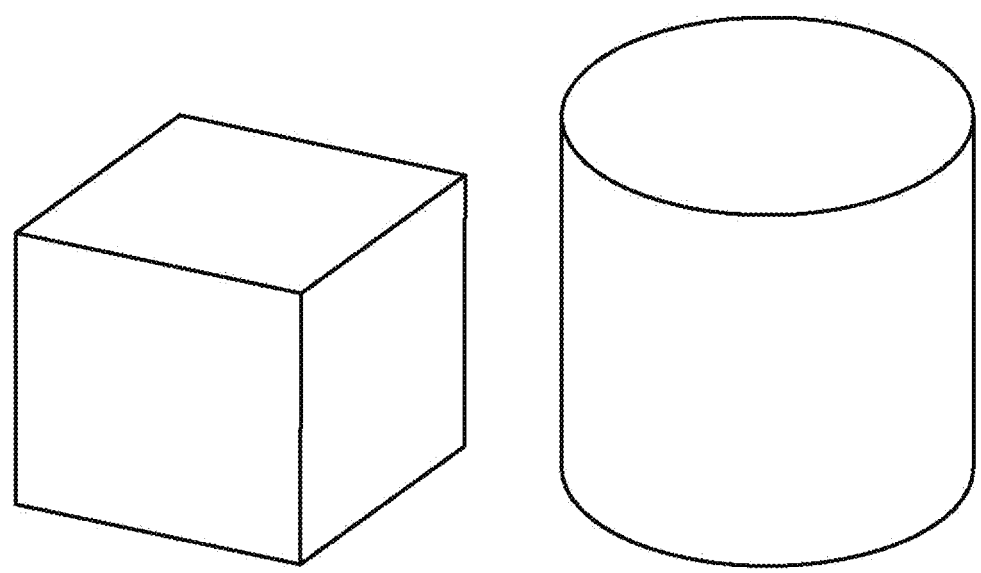
FIG. 11 is a perspective view of examples of carved Tagua shapes.

Processing the dental device material derived from the Tagua nuts includes the steps of shelling and curing the nuts by dehydration or desiccation. Dehydration or desiccation may be achieved wherein the nuts are dried at ambient conditions or accelerated using industrial equipment to rapidly drive off water to a desired level of dryness. Such equipment is well known in the foods industry. The point whereupon the nuts are sufficiently dehydrated for manufacturing dental devices is at the point of comparable hardness of the natural dentin part of a tooth. Standard testing equipment to makes such measurements includes an Instron® Device. This device may be set to measure compressive strength in Pascals that is defined as the value of uniaxial compressive stress necessary to achieve complete failure of the material. Other methods of testing hardness include the Mohs Hardness method. The Mohs Scale of mineral hardness characterizes the scratch resistance of various minerals through the ability of a harder material to scratch a softer material. The Mohs Hardness of dehydrated Tagua is roughly the equivalent to the Mohs Hardness of natural tooth dentin, ranging between 2.5 and 4 on the Mohs Hardness scale. Upon reaching compressive strength comparable to the primary dentin subsurface part of a natural tooth, the nut meat FIG. 9 is processed and shaped into blocks, or other shapes (FIG. 11), that are of certain standard dimensions that are equivalent to those of the standard artificial material currently used in the computer aided design or CAD and manufacturing of dental prostheses.

Figure 10:
FIG. 10 is the chemical formula for hydroxylapatite.

Among the systems known to those skilled in the art of dental device manufacturing is the Chairside Economical Restoration of Esthetic Ceramics™ Series including the CERECTMAC dental milling device. Such milling devices carve blocks of ceramic, composite, or other suitably hard material that are made in such dimensions as to fit in the milling compartment of the machine. The milling device fashions a product of certain size and quality based upon a computer generated 3 dimensional rendering of a particular patient's data. The dehydrated Tagua nut endosperm is preliminarily shaped according to the requirements for use in the CEREC device, or any other brand of milling device, in such a way that a uniform and consistently solid piece in the desired shape and dimensions is produced without any of the naturally occurring gaps or crevices found in the nut. The pieces of Tagua may at this stage of production be treated in one of several ways with the mineral hydroxylapatite, FIG. 10, which is a naturally occurring mineral that is a primary element in human teeth and bone. One method of treating the dehydrated Tagua endosperm is to bathe the Tagua within a solution of hydroxylapatite under such conditions that achieves a suitable coating and desired hardening of the surface. Hydroxylapatite, also called hydroxyapatite (HA), is a naturally occurring mineral form of calcium apatite with the formula $Ca_5(PO_4)_3(OH)$, but is usually written $Ca_{10}(PO_4)_6(OH)_2$ to denote that the crystal unit cell comprises two entities. Hydroxylapatite is the hydroxyl end member of the complex apatite group. The OH— ion can be replaced by fluoride, chloride or carbonate, producing fluorapatite or chlorapatite. It crystallizes in the hexagonal crystal system. Pure hydroxylapatite powder is white. Naturally occurring apatites can, however, also have brown, yellow, or green colorations, comparable to the discolorations of dental fluorosis. Alternative coating methods can be used that involve adhesion or admixture of the Tagua endosperm with the hydroxylapatite. A thermal or plasma surface treatment method may be used for example. Moreover, the treatment may also be made, or repeated, after the final dental prosthetic has been carved. Such treatment is used when additional hardness or other qualities that result from the treatment are desired.

Pulverization of dehydrated Tagua provides for later reconstitution of the material in various admixtures with hydroxyapatite such that desired qualities of size, shape, and hardness may be achieved. Various standard chemical treatments can be applied to adjust qualities of size, color, and hardness.

Figure 12:
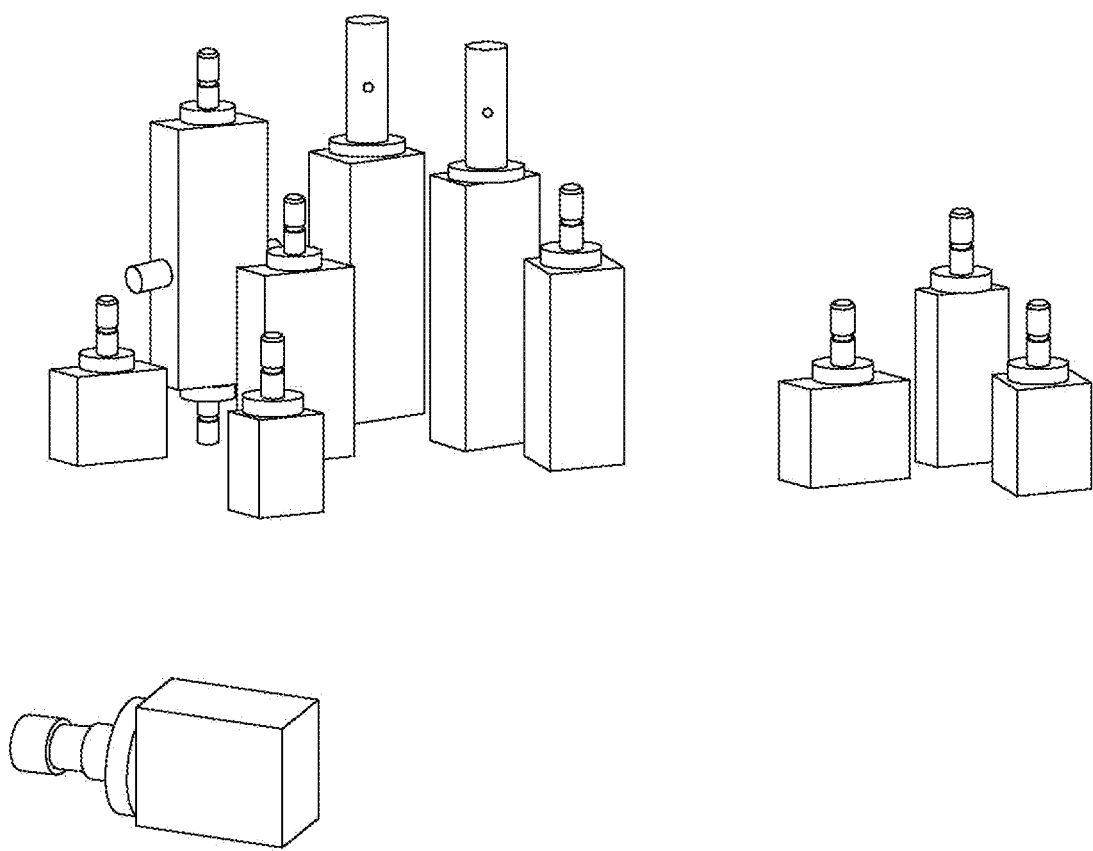
FIG. 12 is a perspective view of examples of final tagua shaped pieces ready for milling.
Figure 13:
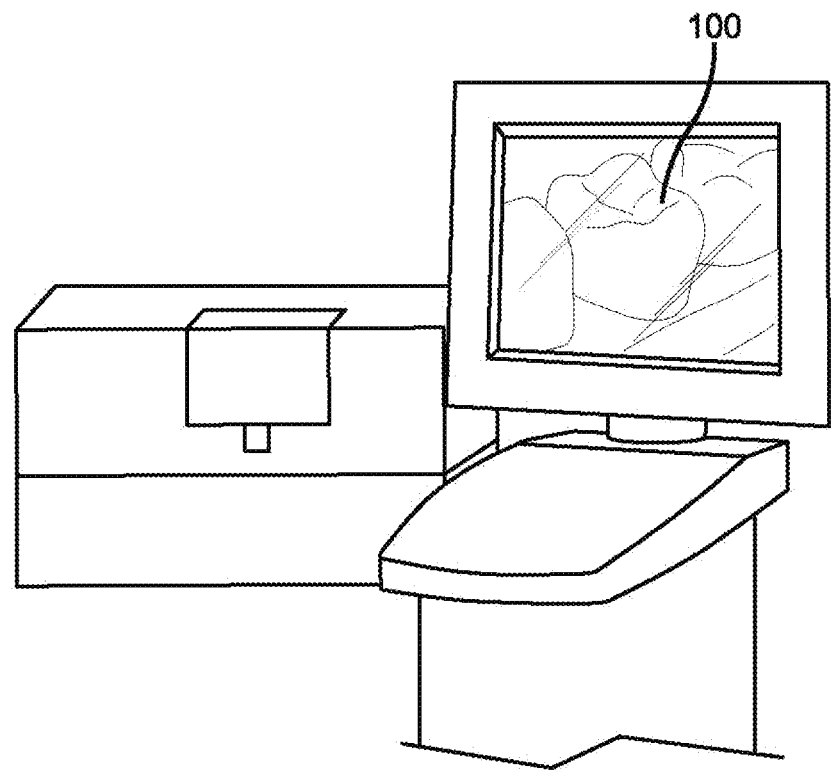
FIG. 13 is a perspective view of an example CAD/CAM "CEREC" Dental Milling Device.

Before placing the dehydrated Tagua nut endosperm into the CEREC or other milling device, a standard abutment or stem may be attached to the piece so that it can be held and manipulated by the device during the milling step (FIG. 12.) Then, the appropriately sized and shaped piece that is suitable to produce the desired prosthetic for given patient is carved in accordance with the computer assisted design data related to the patient using the milling device (FIG. 13), so as to be capable of attachment to a dental implant.

Figure 14:
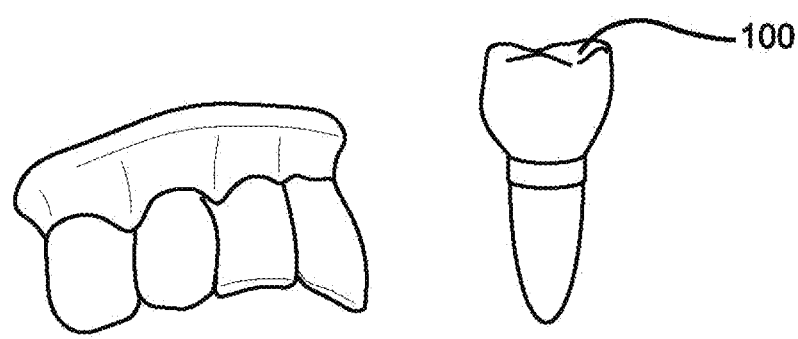
FIG. 14 is a perspective view of examples of finished dental prostheses.

The resulting prosthetic (FIG. 14) is then attachable to a patient's standard implant, which may be of any type. Alternatively, the prosthetic can be fitted to cap a broken tooth by mounting upon a suitably prepared fractional part of an original remaining tooth or teeth. The resulting prosthesis may be of any type, without limitation to, a cap, crown, bridge, partial, or complete denture set. The prosthetic need not attach permanently to implants, as when comprising a removable denture set or bridge for example.

Because the dehydrated endosperm of the Tagua nut, while sufficiently hard, is not superfluously hard in comparison to natural teeth as are the typical ceramic and composite materials ordinarily used by dental milling devices, the carving bits need changing less frequently. What's more, less expensive carving bits may be used in place of the diamond bits otherwise needed.

It is apparent that the sequence of steps involved here may be altered and that other vegetable material of the same genus and species may be substituted for the Tagua nut endosperm without departing from the spirit and scope of the invention. The prostheses contemplated can also be hand carved, using standard power or hand carving tools, both during the fabrication stage and for the purpose of making fitting adjustments.

In another embodiment, the tagua material may be processed as follows. Processing the dental device material derived from the tagua nuts includes the steps of shelling, and curing the nuts by dehydration or desiccation. Dehydration or desiccation may be achieved wherein the nuts are dried at ambient conditions or accelerated using industrial equipment to rapidly drive off water to a desired level of dryness.

A sustainable method of doing business leverages the natural qualities of hardness, color, shape, and size of a plant material, as an alternative to artificial dental materials, so as to minimize the amount of energy used and reduce waste resulting from production. It is also directed at a method of processing dried endosperm of tagua nuts for use in CNC Milling Machines to make customized dental prostheses.

Figure 15:
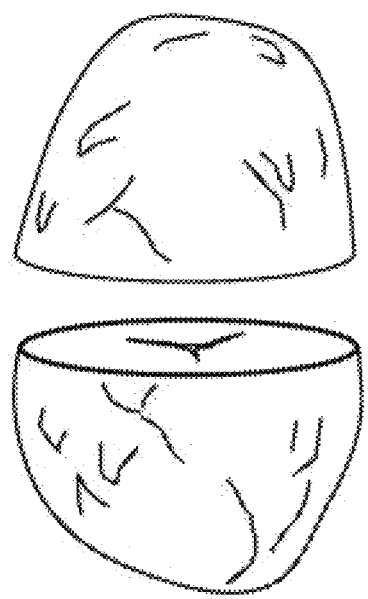
FIG. 15 is an exemplary illustration of a dehydrated and denuded tagua nut that has been cut into two hemispheres.
Figure 16:
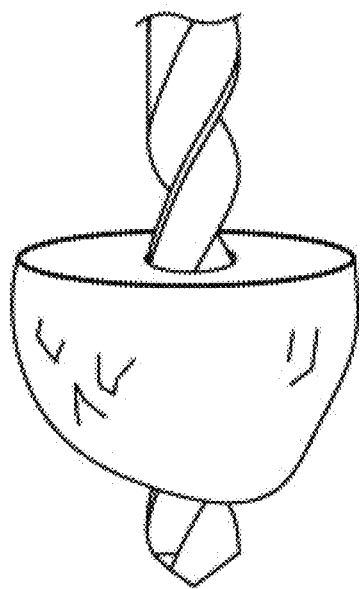
FIG. 16 is an exemplary illustration of making a boring in a hemisphere of a tagua nut.

In an embodiment, a dehydrated tagua nut that has been denuded of the outer brown skin is cut into two hemispheres, as illustrated in FIG. 15. Cutting the nut in this way exposes the irregular shaped hollow center area which is surrounded by a hemisphere of endosperm that is suitable for milling as denture and crown material. The center empty core may be modified by a boring made at some angle vertical to the initial cut made at this step, as illustrated by FIG. 16. This boring renders the irregular jagged character of the hollow core of the nut smooth and uniform in surface quality. The boring is made to pass through the surface of the hemisphere such that a bowl shaped ring of endosperm is provided without crevices. In some instances the boring is done using a boring bit with a rounded top so that the hemisphere is not perforated. In that case, the boring step produces a bowl shaped piece of endosperm with an interior surface without crevices. Other shapes and degrees of pre-forming can be achieved alternatively as a given case may require. Alternate means of carving the endosperm to remove irregularities and to better conform the tagua pieces to the human jaw and palette may be used. Mechanical, chemical, sonic, and photonic methods can be applied individually or in combination to modify the shapes and sizes required for use in milling devices. The cutting and shaping of the tagua nut as described may be done by computer assisted means.

By processing the nut in this way, the endosperm is rendered uniform in material quality and in a shape that conforms generally to the arc and slope of a patient's upper or lower set of natural teeth, as illustrated by FIG. 17.

As illustrated in FIG. 18, the ring or bowl is cut in half such that at least a part of an upper or lower denture can be milled from the resulting pieces with minimum processing and waste. A smaller segment of the bowl or ring can be cut out to provide material pre-cut for milling into a partial set of dentures or for a segment of a full set made of the smaller cuts in combination. A single cap or bridge can likewise be milled from the smaller fractional segments.

Minor software programming changes may be provided at this point so that existing CNC milling devices can receive the modified shapes and sizes for final milling.

At this stage of processing, the endosperm is milled with the aid of a computer processor to fashion a particular patient's denture, or other prosthetic, by applying patient specific data such as jaw shape and size dimensions; together with the desired structural and cosmetic aspects of the final prosthetic to be milled.

In an embodiment, dentists provide the data about the patient specific denture dimensional requirements together with cosmetic specifications to the milling facility over a network such as the Internet. The computer assisted milling of the pre-formed tagua segments into the dental prothesis is then completed at the facility and shipped to the dentist or customer. Alternatively, the milling step can be done right at the dentist's office if suitable equipment is present there.

Data about the patient's mouth may be measured using manual or computer assisted means such as a scanning device. Alternatively, the data can be derived by other imaging methods like an MRI. However measured, the specific individual patient data is provided to a CNC Milling Machine such as a CEREC Device and a customized final dental prosthetic, as illustrated in FIG. 19 is fashioned by computer assistance.

This method leverages the natural size and curvature of the tagua nut which approximates to the general arc size, curvature, and quasi-bowl shape of the human jaw and palette. The method minimizes processing and resulting energy use in the production of the prosthetic. Moreover, the tagua material is an entirely natural renewable resource that is of sufficient hardness and impermeability for ready use as denture material after appropriate treatment.

After the final prosthetic has been carved in accordance with the particular patient's data, additional qualities may be provided to the tagua material by use of natural biocompatible means and materials. For example, naturally produced mussel or barnacle adhesive may be used to add hydroxyapatite as an enamel. This material may be added to provide additional degrees of hardness and insolubility. Such additional qualities may be desirable when the prosthesis is to be permanently fixed to dental implants. Any other biocompatible means of adding additional qualities to the tagua can also be used. A dopamine solution can be used to adhere hydroxyapatite or other natural minerals or material.

In an embodiment, the carved tagua material is dipped directly into an aqueous dopamine solution at pH 8.5. Autopolymerization occurs and the tagua substrate is thereby coated with a polydopamine film up to 50 nm thick. The polydopamine film is surface-active and readily adheres to hydroxyapatite which is then provided for coating the treated tagua by either direct addition of the mineral to the surface or by precipitation out of a solution, such as simulated body fluid.

Additional steps may be performed to regulate the formation of the hydroxyapatite enamel coating which include the placing the protein amelogenin in the solution with hydroxyapatite which regulates the initiation and growth of hydroxyapatite crystals during the mineralization of the enamel.

Temporary caps that are to be mounted on impaired teeth may be rendered with or without additional treatment of the milled tagua prosthesis.

The steps included here can be altered, and various modifications can be made to the method without departing from the scope of the invention. There are a variety of ways that the natural qualities of size and shape of the tagua nut can be leveraged by preforming and treating to enhance the economic use of the material without departing from the scope of this invention. The nuts can be fractionally cut into a variety of to be standardized units that meet the demands of single caps, bridges, partial, or full denture sets. The embodiment outlined herein is just one example of how the natural qualities of the tagua material can be economically and efficiently modified to create a dental prosthesis in a way that is sustainable, biocompatible, and without significant waste.

A sustainable green business is attained by the practice of the methods here that provides a more biocompatible dental prosthesis without any adverse impact on patient health in contrast to the potentially toxic elements, byproducts, and waste related to the manufacturing of other currently used ceramic, composite, artificial products.

EXAMPLES

In Examples 1 and 2 deposition of hydroxylapatite with a non-thermal plasma deposition technique and device was demonstrated.

Example 1

Figure 6:
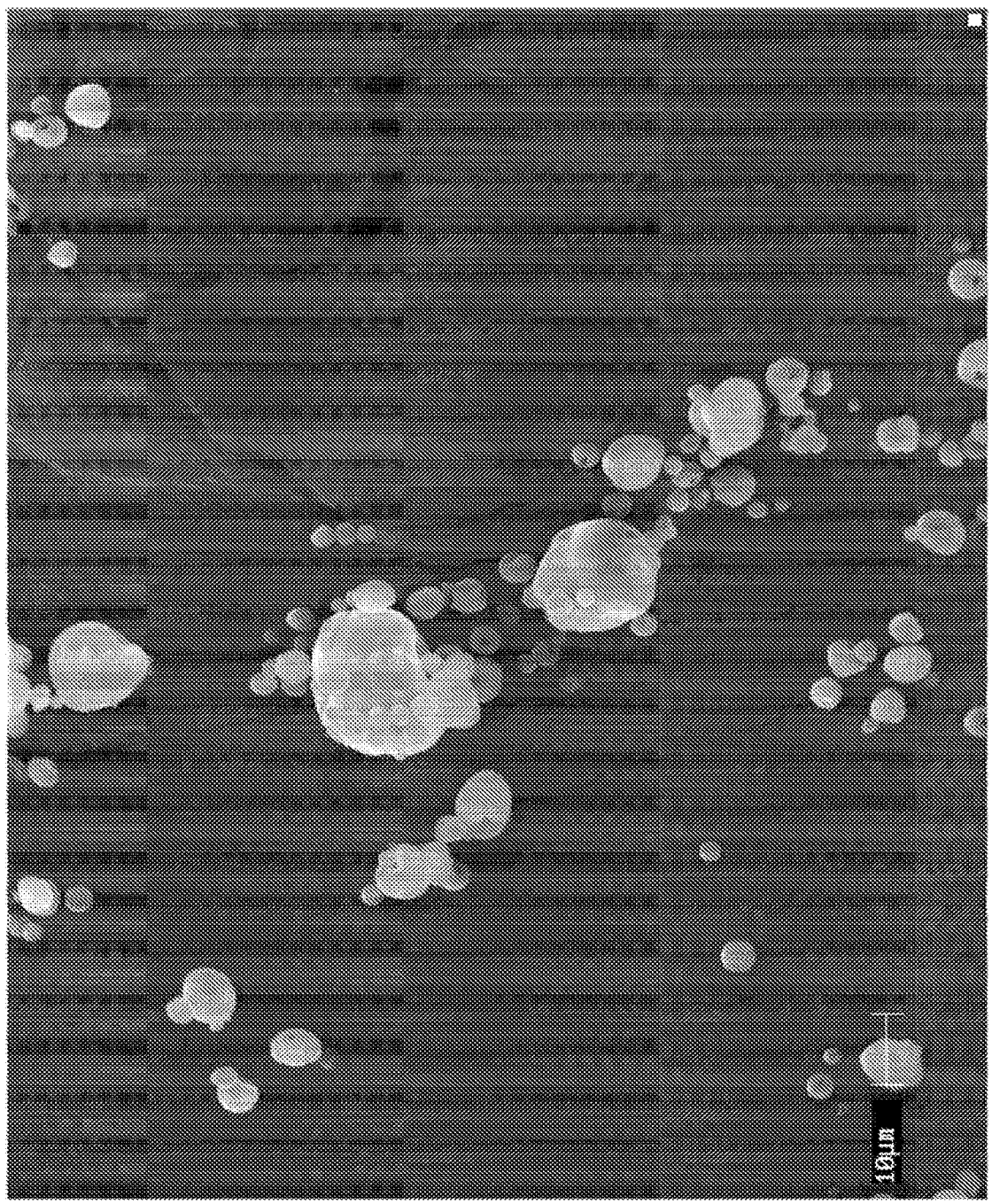
FIG. 6 is an SEM photo of non-thermal plasma deposited hydroxylapatite on a tooth substitute substrate.

FIG. 6 shows an SEM photo that shows the hydroxylapatite restoration material deposited on and affixed to a Tagua surface, which is known to have similar properties to a human tooth. (See U.S. 2013/0224684, which is incorporated herein by reference for all purposes, and the content of which is partially included in this application.)

Example 2

Figure 7:
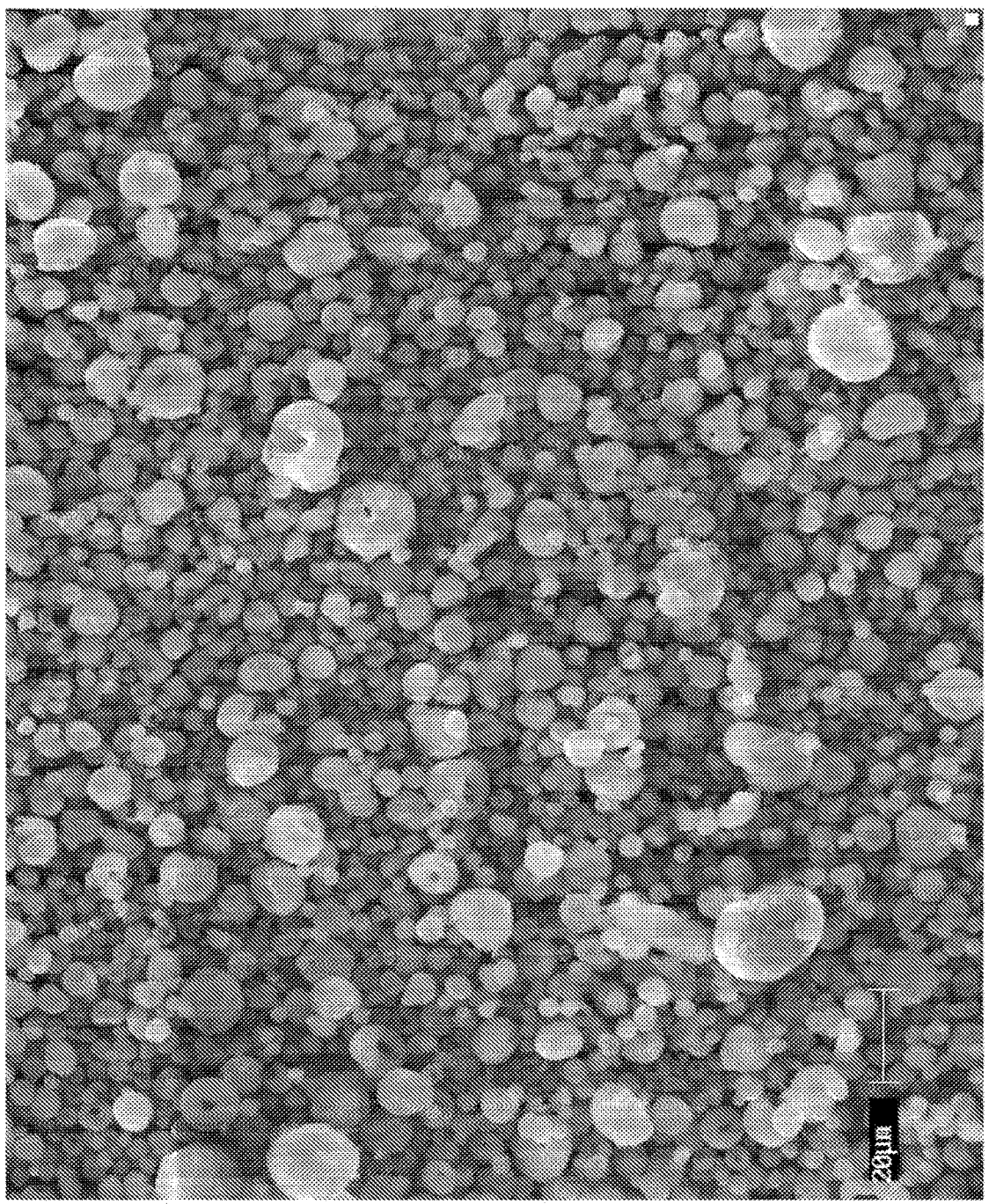
FIG. 7 is an SEM photo of several layers of non-thermal plasma deposited hydroxylapatite.

FIG. 7 is an SEM photo showing the hydroxylapatite crystals piling up in a significant thickness, such as would be useful to restore a damaged portion of tooth or bone by filling in a cracked, chipped, or otherwise damaged area.

Surprisingly, it was discovered that exciting the hydroxylapatite with a non-thermal plasma device produced new crystal growth in the deposited hydroxylapatite. This was observed in the figures as indicated by the angular crystalline features on the spherical particles and among them. This indicated new crystal growth and showed basic adhesion of the new crystals to old.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. The scope of the invention is not to be determined by the specific examples provided above but only by the claims below. In other instances, well-known structures, devices, and operations have been shown in block diagram form or without detail in order to avoid obscuring the understanding of the description. Where considered appropriate, reference numerals or terminal portions of reference numerals have been repeated among the figures to indicate corresponding or analogous elements, which may optionally have similar characteristics.

It should also be appreciated that reference throughout this specification to "one embodiment", "an embodiment", "one or more embodiments", or "different embodiments", for example, means that a particular feature may be included in the practice of the invention. Similarly, it should be appreciated that in the description various features are sometimes grouped together in a single embodiment, figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

What is claimed is:

1. A prosthetic comprising:
a sustainable material derived from a nut of a tree from the Arecaceae family shaped and subjected to a treatment to affect a physical characteristic and suitable for replacement of a non-sustainable metal, ceramic, porcelain, plastic or composites of any of these;
wherein the sustainable material is pulverized and reconstituted.

2. The prosthetic of claim 1, wherein the prosthetic is at least a portion of a tooth or bone.

3. The prosthetic of claim 1, wherein the treatment results in a modification of the physical characteristic of solubility or hardness.

4. The prosthetic of claim 1, wherein the sustainable material is configured as a human prosthetic.

5. The prosthetic of claim 1, wherein the nut is pulverized and reconstituted then subjected to the treatment.

6. The prosthetic of claim 5, wherein the prosthetic is at least a part of a tooth or bone.

7. A sustainable material comprising:
a nut material of the Arecaceae family shaped and treated with radiation to affect a physical characteristic thereof;
the shaped and treated nut material being suitable for replacement of a non-sustainable metal, ceramic, porcelain, plastic or composites of these materials;
wherein the nut material is pulverized and reconstituted.

8. The sustainable material of claim 7, wherein the nut is of a tree of the *Phytelephas* genus.

9. The sustainable material of claim 7, wherein the nut material is combined with a mineral.

10. The sustainable material of claim 9, wherein the mineral is in a powder form or a solution including a powder form of the mineral.

11. The sustainable material of claim 7, wherein the nut has been pulverized and reconstituted in admixture with a mineral.

12. The sustainable material of claim 11, wherein the mineral is hydroxyapatite.

13. A composite material comprising:
a nut material derived from a nut of the Arecaceae family, the nut material combined with a mineral to affect a physical characteristic thereof;
wherein the nut material is suitable for replacement of a metal, ceramic, porcelain, plastic or composites of these materials;
wherein the nut material is pulverized and reconstituted with the mineral.

14. The composite material of claim 13, wherein the mineral is hydroxyapatite.

15. The composite material of claim 13, wherein the composite material is treated with radiation.

16. The composite material of claim 13, wherein the mineral is in powder form.

17. A sustainable material comprising:
a nut material of the Arecaceae family;
the nut material being suitable for replacement of a non-sustainable metal, ceramic, porcelain, plastic or composites of these materials;
wherein the nut material is pulverized and reconstituted and is configured as a human prosthetic;
wherein the sustainable material further comprises a mineral and the mineral is hydroxyapatite.

18. The sustainable material of claim 17, wherein the nut material of the Arecaceae family is tagua.

19. The sustainable material of claim 17, wherein the nut material is a suitable for replacement for plastic.

20. The sustainable material of claim 17, wherein the nut material is a suitable for replacement for ceramic.

* * * * *